United States Patent [19]
Dubin et al.

[11] Patent Number: 5,922,531
[45] Date of Patent: Jul. 13, 1999

[54] POLYELECTROLYTE TREATED GLASS FOR ENZYME IMMOBILIZATION AND PROTEIN PURIFICATION

[75] Inventors: Paul L. Dubin; Yingfan Wang, both of Indianapolis, Ind.

[73] Assignee: Advanced Research and Technology, Bloomington, Ind.

[21] Appl. No.: 08/916,491

[22] Filed: Aug. 22, 1997

Related U.S. Application Data

[63] Continuation-in-part of application No. 08/263,041, Jun. 21, 1994, Pat. No. 5,834,271.

[51] Int. Cl.[6] ............................... C12Q 1/00; C12Q 1/37; C12N 11/00; C12N 9/00
[52] U.S. Cl. ............................... 435/4; 435/23; 435/174; 435/183; 501/11; 501/53
[58] Field of Search ............................... 435/4, 23, 174, 435/183; 501/11, 53

[56] References Cited

U.S. PATENT DOCUMENTS

| | | | |
|---|---|---|---|
| 4,102,746 | 7/1978 | Goldberg | 435/4 |
| 4,169,014 | 9/1979 | Goldberg | 435/4 |

OTHER PUBLICATIONS

Kokufuta, *Prog. Polym. Sci.* vol. 16, Issue 4: pp. 647–697 (1992).
Dubin, *Industrial Bioprocessing* (Oct. 1996).
Fleer, Special Publication *Royal Society of Chemistry* pp. 34–46 (1991).
Laat et al., *Colloids and Surfaces:* pp. 61–71 (1995).
Rawls, *C&EN* pp. 27–28 (Apr. 28, 1997).
Wang et al., presented at 212th ACS Meeting (Aug. 26–28, 1996).
Wilson et al., *American Chemical Society* pp.1–51 (1990).
Braude et al; Biochimica et Biophysica Acta, vol. 580, pp. 15–23 (1979). Month Not Available. Please Print.

*Primary Examiner*—Louise N. Leary
*Attorney, Agent, or Firm*—Leydig, Voit & Mayer, Ltd.

[57] ABSTRACT

Materials and methods for selectively adsorbing proteins are disclosed. Under the invention, controlled pore glass is treated with a polyelectrolyte layer which comprises at least one polymer having a cationic portion which is electrostatically attracted to the porous outer surface of the glass. The constituents of the polyelectrolyte are preferably selected to have an affinity for the predetermined protein to facilitate adsorption thereof on the polyelectrolyte treated glass. Advantageously, the materials of the present invention can be utilized to immobilize enzymes and also to separate proteins from other components in a medium.

21 Claims, 9 Drawing Sheets

POLYELECTROLYTE TREATED GLASS FOR ENZYME IMMOBILIZATION AND PROTEIN PURIFICATION

CROSS-REFERENCE TO RELATED APPLICATION

This application is a continuation-in-part of application Ser. No. 08/263,041, filed Jun. 21, 1994, now U.S. Pat. No. 5,834,271, entitled Enzyme Compositions and Use Thereof.

This invention was made with government support under Grant Number DMR-9311433 awarded by the National Science Foundation. The government has certain rights in the invention.

BACKGROUND OF THE INVENTION

The present invention relates generally to materials and methods for adsorbing macromolecules such as enzymes and other proteins, as might be particularly useful in enzyme immobilization and protein separation.

Enzymes and other proteins are highly useful materials and are used in numerous ways. For example, in order to capitalize on the ability of enzymes to catalyze almost any type of chemical reaction with extraordinary specificity and efficacy, one significant use for enzymes is as catalysts in industrial-scale chemical synthesis. Because enzymes are difficult to recover and are highly susceptible to denaturation by chemical or physical factors such as pH extremes, temperature and/or the presence of organic materials, it is important that the enzymes be immobilized, or compartmentalized, to enhance their use in bulk chemical synthesis.

Previous attempts to immobilize enzymes to permit their use in industrial reactions have not met with success. One prior approach involved the use of microcapsules to create an outer barrier for protecting the active enzyme therein. The concept of microencapsulation is ill-suited to immobilize enzymes because of insufficient transport kinetics for permitting diffusion of the enzyme in and out of the microcapsule. As a result, the wall or barrier provided by the microcapsule does not provide the enzyme with sufficient exposure to the medium in which it is supposed to act thereby resulting in a loss of enzymatic activity. Other prior approaches included alginate beads, cross-linked polyurethane, starch particles and polyacrylamide gels. Not only are the procedures for forming these materials quite complex, but the materials are soft gels and are therefore not mechanically strong.

A more recent approach for immobilizing enzymes has involved the use of coacervates, which are aggregates of colloidal droplets arising via aggregation primarily through the force of electrostatic attraction. However, the use of coacervates to incorporate enzymes, while not using a capsule, still has not been fully satisfactory. For example, coacervates tend to aggregate and collect into larger particles and are therefore subject to instability. Whereas it is normally desired that the coacervate droplets have a diameter of approximately 1 micrometer, these droplets can undesirably combine to become 10 micrometers or more in diameter. These larger droplets result in a proportionately smaller surface area in which the enzymes can act, and consequently, do not optimize the reaction rates. In addition, the coacervates themselves are somewhat fragile and are not capable of being subjected to, for example, flow-through reactors. Coacervates also do not constitute a versatile design and require low-speed centrifugation for removal.

Another area in which proteins must be adapted for use relates to protein purification or separation in which a target protein is separated from one or more other components such as other proteins or nucleic acids. Prior attempts to purify proteins have involved a large number of steps, often 17 or more steps, to ultimately purify and separate a target protein. These numerous steps can include gross filtration, centrifugation, settling, salting out, two-phase extraction, one or more chromatography steps, or other steps. For example, a cell crush may initially be purified to remove some components, such as lipids, sugars, particulates, and cell debris. However, removal of a target protein from other proteins and nucleic acids is still time-consuming, expensive and complex because of the requirement of numerous steps and can be diluting. Strictly by way of example, recombinant DNA techniques that utilize yeast or bacteria in making human insulin result in a cell crush that requires a number of purification steps, ranging from coarse filtration to very detailed fine tuned chromatography that greatly contribute to the expense of the final product.

From the foregoing, it will be appreciated that there exists a need in the enzyme immobilization art for an enzyme substrate that supplies sufficient mechanical strength while permitting the enzyme to be highly exposed to the medium in which it is supposed to act. There also exists a need for such an enzyme substrate where there is no barrier or wall that requires diffusion in and out of the barrier that causes a loss of enzymatic activity. It will also be appreciated that there exists a need in the protein purification art for methods and materials for purifying and separating a target protein from other components present in a medium that does not require numerous steps.

SUMMARY OF THE INVENTION

The aforesaid problems are solved, in accordance with the present invention, by materials and methods for adsorbing predetermined enzymes and other proteins selectively. Under the present invention, glass particles having a porous outer surface, or alternatively, silica particles, are coated with a cationic polyelectrolyte that is selected to adsorb predetermined proteins such as enzymes.

Advantageously, the glass or silica particles impart sufficient mechanical strength and the presence of the polymer on the outer surface of the glass or silica permits the enzyme to be highly exposed to the medium in which it is supposed to act to permit rapid catalytic action. The protein is adsorbed to the polyelectrolyte-layered glass or silica particles by long-range electrostatic forces that are sufficient to maintain the enzyme within the solid matrix while still allowing full solvation and considerable mobility so as to not impair its enzymatic functions. In addition, the polyelectrolyte-layered glass or silica particles, with or without the proteins, provide very high mechanical strength and therefore permit use under high pressure conditions and flow rates in continuous processes and are also relatively inexpensive to utilize. Remarkably, the polyelectrolyte layer is quite stable, even though it is bound by noncovalent forces, and is reconstituted upon washing, drying and rehydration. Also, the protein does not precipitate in use and is not exposed to a nonaqueous solution and will therefore not become denatured. Advantageously, the protein such as an enzyme can be easily separated from the matrix after use, for example, by subjecting the protein adsorbed polyelectrolyte-treated glass or silica to variations in pH, accompanied as necessary by low-speed centrifugation, depending upon the size of the glass or silica particles.

One significant utility for the present invention relates to enzyme immobilization by adsorbing the enzyme on the polyelectrolyte treated glass or silica particles. The enzymes can be those used to catalyze bulk chemical synthesis. In this regard, the enzymes are exposed to the desired reaction medium and do not have to diffuse in and out of an outer wall or barrier. Further, the enzymes are supported by a substrate having sufficient mechanical strength to permit the use of the enzymes in a variety of reaction environments. Also, unlike the coacervates of the prior art, the glass or silica particles will not agglomerate into larger particles and will therefore maintain a desired surface area relative to the volume of the reaction medium.

The polyelectrolyte-treated glass or silica particles of the present invention can also be used to selectively separate a predetermined protein from a medium containing other components, such as other proteins and nucleic acids. In particular, a medium may contain a number of components that must be removed to purify the medium. While some of the undesirable components are removed through other means, such as settling, extraction, or salting out, the target protein may still be in a medium that contains other proteins and/or nucleic acids. While the prior art required numerous steps, such as one or more chromatography steps, in order to isolate the target protein, the present invention permits separation of the target protein with greater ease. The adsorption of the target protein, relative to other competing species, including, for example, other proteins, DNA or polysaccharides, can be modulated by pH and ionic strength. For example, the present invention can be used to discriminately isolate and adsorb a preselected protein type present in a cell crush or subsequent downstream resulting mixture by tailoring the polyelectrolyte layer to have a portion that will have an affinity for the target protein while rejecting and not binding to the nontarget proteins or nucleic acids that might also be present in the crush.

The present invention will be more fully understood upon reading the following Detailed Description of Preferred Embodiments in conjunction with the accompanying drawings.

DETAILED DESCRIPTION OF THE PREFERRED EMBODIMENTS

The following portion of the specification, taken in conjunction with the drawings, sets forth preferred embodiments of the present invention. Embodiments of the invention disclosed herein include the best mode contemplated by the inventors for carrying out the invention in a commercial environment, although it should be understood that various modifications can be accomplished within the parameters of the present invention.

In accordance with the present invention, glass particles having a porous outer surface, for example, controlled pore glass particles, or silica particles are treated with a polyelectrolyte layer in order to selectively adsorb predetermined proteins. The glass particles can be in a variety of forms, including, but not limited to, spheres, beads and pellets. The polyelectrolyte layer includes at least one polymer that includes a region having a net positive charge that will electrostatically be attracted to the outer glass surface of the particles at moderate to high basic conditions. The polyelectrolyte layer is also tailored to attract the predetermined protein by including a molecular portion that has an affinity for the protein, as described in more detail hereinbelow.

The size of the glass particles can vary, but preferably have a diameter ranging from approximately 1 micrometer to 1 millimeter, and more preferably ranging from approximately 1 micrometer to approximately 60 micrometers. The optimum size of the glass particles depends on the particular application desired. While smaller glass particles provide a larger surface area relative to the surrounding volume of the medium, smaller glass particles are also more buoyant and suspendable in the medium and are thus susceptible to hydrodynamic forces. As a result, if the particles are to be used in connection with a column in which they will packed, smaller particles might be undesirable because flow processes will be impeded, thereby negating the prospects of enhanced reaction rates potentially delivered by the larger surface area supplied by the smaller glass particles. Conversely, if the desired application does not require operation of a column where rapid flow is desired, smaller particles may be selected to take advantage of the enhanced surface area and concomitantly enhanced reaction rates.

Silica particles, meanwhile, can be quite smaller than glass particles. For example, silica particles under the present invention can preferably range in diameter from about 10 nanometers to about 1000 nanometers. As a result, silica particles are particularly useful in applications where smaller particle size is desired, such as, but not limited to, high resolution chromatography.

The glass particles contain surface pores which facilitate adsorption of the polyelectrolyte layer thereon. More specifically, the pores on the outer surface of the glass particles are essential in enhancing the surface area of the particles. It is to be noted that silica particles can be nonporous by virtue of their smaller size which already furnishes the requisite surface area for enhancing protein activity. Examples of suitable glass particles containing surface pores that are commercially available include Model Nos. "CPG-00500C" and "CPG 00350C" available from CPG, Inc. of Lincoln Park, N.J., as well as Model No. "Native-500-CPG" by Prime Synthesis of Aston, Pa. The controlled pore glass particles under the present invention can be made, for example, by way of a biphasic process. The biphasic process utilizes two different glass types, one that is a softer glass and one that is a harder glass, which are then mixed and heated to vitrify the two glasses together. After the glasses are solidified, they are ground to the desired particle size and etched. Ultimately, the soft glass regions are removed by etching to create pores. These pores are relatively large as compared to the polyelectrolyte and enzyme molecules with which they are to be used in accordance with the present invention.

The polyelectrolyte layer is adsorbed onto the glass through electrostatic attraction. The glass particles contain SiOH groups that constitute a weak acid which ionize at moderate to high pH, most typically from a pH of about 7 to a pH of about 10. As a result, the polyelectrolyte must contain a polymer having a cationic component that is electrostatically attracted to SiOH groups on the glass particle surface. In addition to the cationic charge, the polyelectrolyte must also contain a sufficient molecular weight to satisfactorily adhere to the glass particles. While the molecular weight of the polyelectrolyte can vary significantly, the molecular weight of the polyelectrolyte is typically within a range of from about 20,000 to about 2,000,000, but it is believed that the optimal molecular weight for the polyelectrolyte ranges from about 200,000 to about 400,000.

The polyelectrolyte can include one or more polymers including copolymers. In particular, the constituents of the polyelectrolyte are tailored specifically to adsorb certain enzymes or to target proteins while rejecting nontarget molecules. Accordingly, the repeat units in the polymer structure are important because, by their nature, different repeat units are better equipped to discriminately attract different target proteins. The variety of polymer structures constitutes variables or parameters which are important criteria for selecting the target proteins. Examples of important structural parameters include, but are not limited to, polymer linear charge density, hydrophobic uncharged polymer repeat units or residues, hydrophilicity, anionic residues, nonionic residues, combinations thereof, or the population of other repeat units or residues that would be utilized as an affinity group for attracting the desired proteins. For example, with regard to linear charge density, the distance along the polymer backbone between charge groups can be important in protein discrimination.

By way of example, poly(diallyldimethylammonium chloride) ("PDADMAC") is a homopolymer which may be suitable for some applications. Other examples of satisfactory polyelectrolytes include, but are not limited to, any of the group consisting of poly (methacrylamidopropyltrimethylammonium chloride) (PMAPTAC), poly(L-Lysine), poly(L-Arginine), poly(4-vinylpyridinium salt), polyethyleneimine (PEI), or cationic equivalents of similar or related polymers. However, one of ordinary skill in the art will appreciate that it is possible to provide a number of different polymers and copolymers that could have a cationic portion as well as, for example, a nonionic and hydrophilic portion, or alternatively, a nonionic and hydrophobic repeat unit or yet other selected varied repeat units.

Referring to the thickness of the polyelectrolyte layer when disposed on the glass particles, the layer is preferably at least monomolecular in thickness, more preferably ranging from about 5 nanometers to about 20 nanometers, although other variations can be utilized. The range of 5 to 20 nanometers is most desired because thicker layers might begin to impede diffusion of proteins in and out of the layer so as to make the protein less accessible to the reaction medium. Conversely, if the polyelectrolyte layer is too thin, then the capacity for adsorbing proteins can become undesirably small.

In preparing the present invention, molecular weight, ionic strength, polymer concentration and pH are all contributory factors in the molecular adhesion of the polymer to the glass and, in turn, the protein to the polymer layer on the glass. With regard to ionic strength, a salt such as NaCl, $NaNO_3$, KCl, $Na_2SO_4$ or, $KNO_3$ or other salt, is provided to water to create a solution having an ionic strength ranging from about 0.01 molar (moles of salt/liter of water) to about 0.2 molar. In addition, an acid or base is added, as needed, in order to regulate the pH of the solution as desired. Preferably, the pH of the solution will provide a moderate to high pH such as a pH from approximately 7 to approximately 10. Examples of acids that can be used include, but are not limited to, HCl, $H_2SO_4$, $HNO_3$, $H_3PO_4$ or others. Examples of bases that can be used to regulate the pH of the solution include NaOH, KOH, $NH_4OH$ or others. If the pH is too high and the salt concentration is too low, then the polyelectrolyte polymer would adhere too strongly to the glass particles thereby making adsorption of the desired proteins more difficult at the molecular level. In contradistinction, if the pH of the solution is too low and the salt concentration is too high, then the polyelectrolyte polymer will not adsorb sufficiently to the glass particles. Accordingly, the pH and salt concentration will be selected to permit the polyelectrolyte polymer to adhere molecularly loosely to the glass particles to permit further adsorption of proteins thereon.

Figure 1:
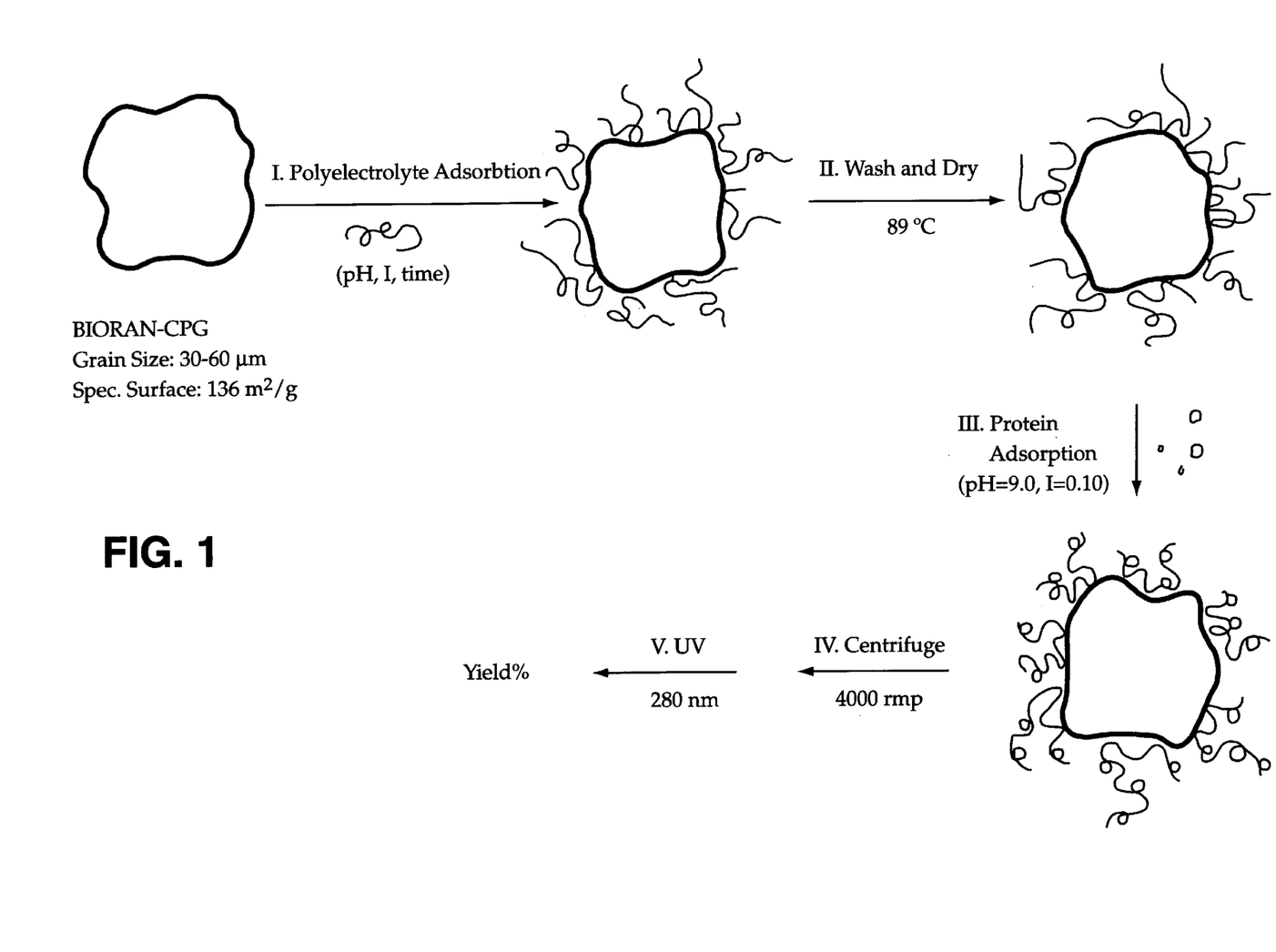
FIG. 1 depicts a schematic process of a typical batch adsorption experiment.

After preparing the solution with the desired concentration of salt and the desired pH adjustment, the polyelectrolyte component can be added to the solution. As indicated earlier, the molecular weight of the polymer can vary from approximately 20,000 to approximately 2,000,000 or higher. Next, the glass particles containing the pores on the outer surface can now be added to the solution, preferably while the solution is stirring. Under the desired conditions, the glass adsorbs the polyelectrolyte polymer and the form in which the polymer is adsorbed at the molecular level is predetermined by the aforementioned conditions. The polyelectrolyte treated glass particles can now be removed from the solution by, for example, settling or centrifugation, depending upon the particle size of the glass. For example, if the glass particles are sufficiently large, settling would be appropriate for removing the treated glass from the solution, but if the glass particles are too small, centrifugation could be utilized to remove the treated glass. The polyelectrolyte treated glass can then be washed to remove excess polyelectrolyte and salt and can then be dried in advance of the desired use in enzyme immobilization or protein purification. FIG. 1 schematically illustrates an exemplary process.

It is to be noted that the glass particles can alternatively be prepared under flow conditions. For example, the controlled pore glass particles can be packed into a column and the polyelectrolyte can be pumped through the packed glass particles while in solution under the desired conditions.

In order to promote a further understanding and appreciation of the present invention and its attendant advantages, the following Specific Examples are provided. It will be understood that these Examples are illustrative and not limiting in nature. It is to be noted that proteins were used without further purification.

EXAMPLE 1

Batch Adsorption

Controlled pore glass (CPG) (30–60 μm grain size, pore diameter 29.4 nm, and 136 m²/g specific surface area) was obtained from Schott Geraete (Mainz, Germany). The CPG was cleaned with 1% SDS at room temperature at pH 9 for 2 hours, washed with Dl water, and dried at 89° C. for more than 12 hours.

This cleaned CPG was then used to adsorb a polyelectrolyte employing different pH, ionic strengths, and adsorption times. Poly(diallyidimethylammonium chloride) (PDADMAC)(Merquat 100, Calgon Corp., Pittsburgh, Pa.) with a nominal molecular weight (MW) of $2 \times 10^5$ and $M_w/M_n > 5$ was dialyzed (molecular weight cutoff=12,000–14,000) and freeze-dried before use. An aqueous solution of the PDADMAC was made at 20 g/L at pH 9.0. The CPG was added slowly into the stirring PDADMAC solution, which was then stirred overnight to reach equilibrium. The solution was centrifuged to isolate the PDADMAC-treated CPG from the PDADMAC solution, and the solid was washed 5 times with deionized (Dl) water before drying at 89° C. for more than 24 hours thus forming dried polyelectrolyte treated porous glass particles in accordance with the present invention.

The polyelectrolyte adsorption effectiveness of such particles in adsorbing protein was studied. Protein binding to polyelectrolyte-treated CPG was performed at pH 9 and ionic strength 0.1, using 100 mg of PDADMAC-CPG in each experiment. The PDADMAC-CPG was added to a protein containing solution, and the solution was centrifuged to remove the PDADMAC-CPG with any protein bound thereof. The protein concentration in the supernatant was then measured by UV at λ 280 nm.

The amount of adsorbed protein was then determined by subtracting the amount in the supernatant from the total.

EXAMPLE 2

Chromatography

The chromatographic system included a Minipump (Milton Roy, St. Petersburg, Fla.), a 100 μl sample loop, a R401 differential refractometer (Waters, Milford, Mass.), and a Kipp & Zonen Recorder (Model BD 112, Delft, Holland).

A stainless-steel column (25 cm×0.5 cm I.D.) was packed with PDADMAC modified CPG prepared in accordance with Example 1 (pH 9, $C_p$=20 g/l, no salt added). The column efficiency was measured to be $2.4 \times 10^3$ plates/meter (measured with $D_2O$). A boric acid —NaOH buffer was used as the mobile phase at selected pH and ionic strength. The flow rate was maintained between 0.5 ml/min and 0.6 ml/min.

EXAMPLE 3

Chromatography (Comparative Example)

A stainless steel column was packed with native CPG in a manner similar to Example 2. Both columns were subjected to Pullulan standards (Shodex standard, P-82, Lot 50501) and were purchased from Showa Denko K.K. (Tokyo, Japan).

The partition coefficient of SEC is defined as:

$$K_{\text{sec}} = \frac{(V_c - V_O)}{(V_t - V_o)} \quad \text{(Equation 1)}$$

where $V_c$ is the retention volume of the solute, $V_o$ is the void volume of the column, and $V_t$ is the total volume of the column. If the column pores are cylindrical, $K_{sec}$ can be simply expressed as:

$$K_{\text{sec}} = \left(1 - \frac{R}{r_p}\right)^2 \quad \text{(Equation 2)}$$

where R is the radius of solute, and $r_p$ is the radius of the pore. The pore radius $r_p$ can then be calculated as the reciprocal of the slope of a plot $K^{1/2}$ vs. R.

Figure 2:
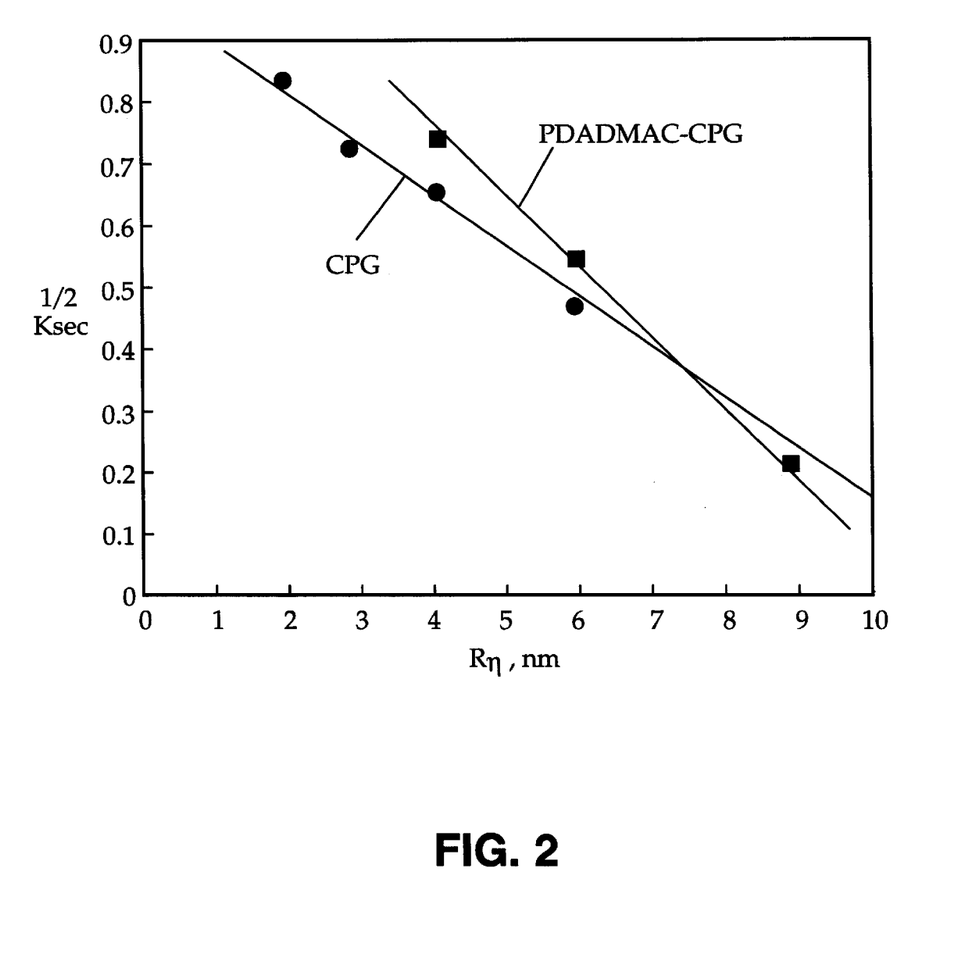
FIG. 2 is a graph of the partition coefficient as a function of the radius of the solute with and without the addition of Poly(diallyldimethylammonium chloride) (PDADMAC) illustrating a Size Exclusion Chromatography (SEC) measurement of pore radius.

FIG. 2 shows a plot of $K^{1/2}$ vs. R for Pullulan standards on both native and polyelectrolyte-treated CPG columns. From equation 2, $r_p$ was obtained as the reciprocal of the slope, with $r_p$=11.4 nm and 8.9 nm, for native and treated CPG respectively. The decrease of $r_p$ after polyelectrolyte adsorption indicates the formation of a polymer layer within the pores, and the 2.5 nm difference may be used to estimate the polyelectrolyte adsorption layer thickness. This method for monitoring polyelectrolyte adsorption suggests the possibility of controlling pore size. The value of $r_p$ should be one measure of the microscopic structure of the adsorbed polyelectrolyte.

EXAMPLE 4

Effect of Preparation pH and Ionic Strength on Protein Removal

We have observed protein binding on polyelectrolyte-treated CPG and the effect of pH, ionic strength, and time on polyelectrolyte adsorption layer ($\delta_H$). In this section, protein chromatographic properties will be interpreted in terms of microscopic structure of adsorbed polyelectrolytes.

Figure 3:
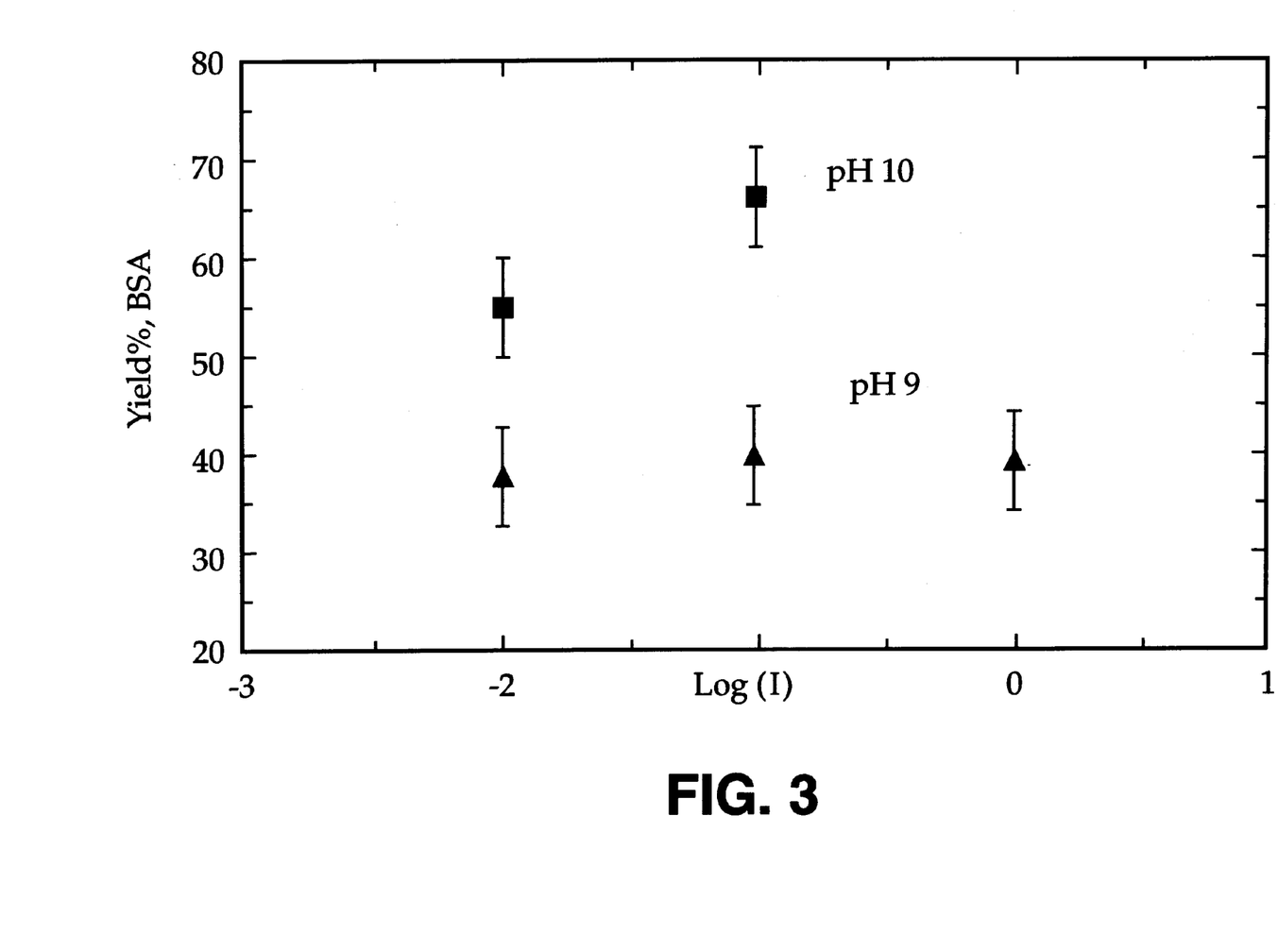
FIG. 3 is a graph of bovine serum albumin (BSA) removal yield by PDADMAC treated controlled pore glass (CPG) at various pH levels and ionic strengths and illustrates the effect of preparation pH and ionic strength on subsequent BSA removal.

FIG. 3 shows the amount of protein removed (yield %) by batch mixing with polyelectrolyte-treated glass. The pH and ionic strengths shown in FIG. 3 represent the conditions that were used to adsorb the polyelectrolyte on the CPG surface, and thus represent different PDADMAC-CPG preparations. Protein binding on polyelectrolyte-treated glass is affected by the initial conditions at which the polyelectrolyte was adsorbed. It is known that the amount of adsorbed polyelectrolyte increases linearly with the surface charge. Consequently, more polyelectrolyte is adsorbed at high pH, and the resultant PDADMAC-CPG removes more protein. On the other hand, preparation ionic strength did not significantly affect subsequent protein binding; this phenomena will be explained below.

EXAMPLE 5

Effect of Preparation Time and Ionic Strength on Protein Removal

Figure 4:
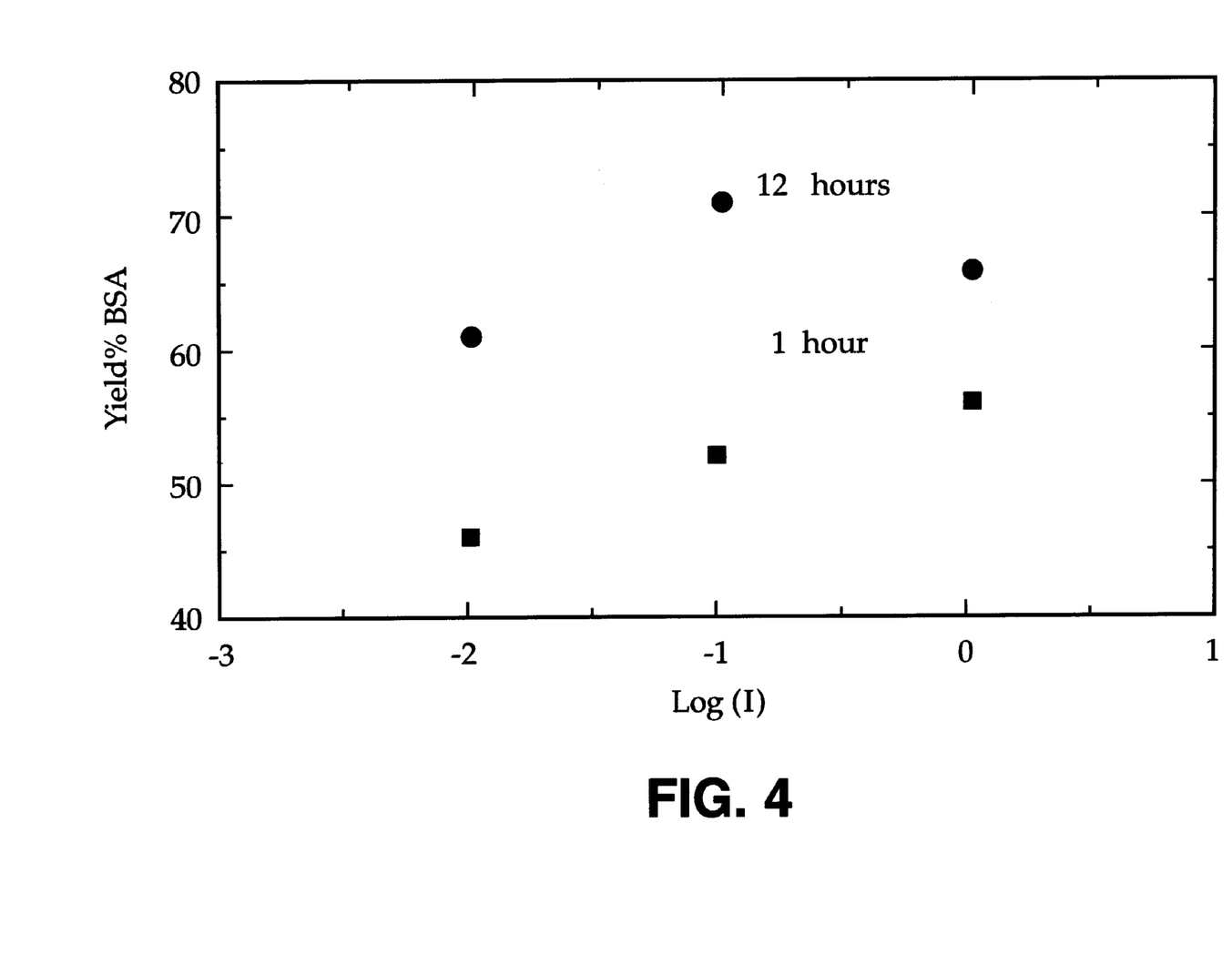
FIG. 4 is a graph of bovine serum albumin removal yield at various exposure time intervals and illustrates the effect of preparation time and ionic strength on subsequent BSA removal by PDADMAC-CPG.

FIG. 4 [PDADMAC adsorption: pH=8.5, Cp=1 g/l, stirring for 12 hours; BSA (Bovine serum albumin, identified hereinafter as BSA, was purchased from Boehringer Mannheim, Indianapolis, Ind., Lot 100062); Protein binding: pH'=9.0, I'=0.10, Cpr=0.10 g/L, 0.010 g PDADMAC-CPG in 0.010 L] shows the effect of preparation time in the polyelectrolyte adsorption step on subsequent protein binding. As seen in FIG. 4, longer mixing time clearly enhances the protein binding process. It has previously been proposed that the amount of PAA adsorbed on BaTiO$_3$ increased over long periods, consistent with the results in FIG. 4.

EXAMPLE 6

Effect of Polyelectrolyte Concentration on Different Protein Removal

Figure 5:
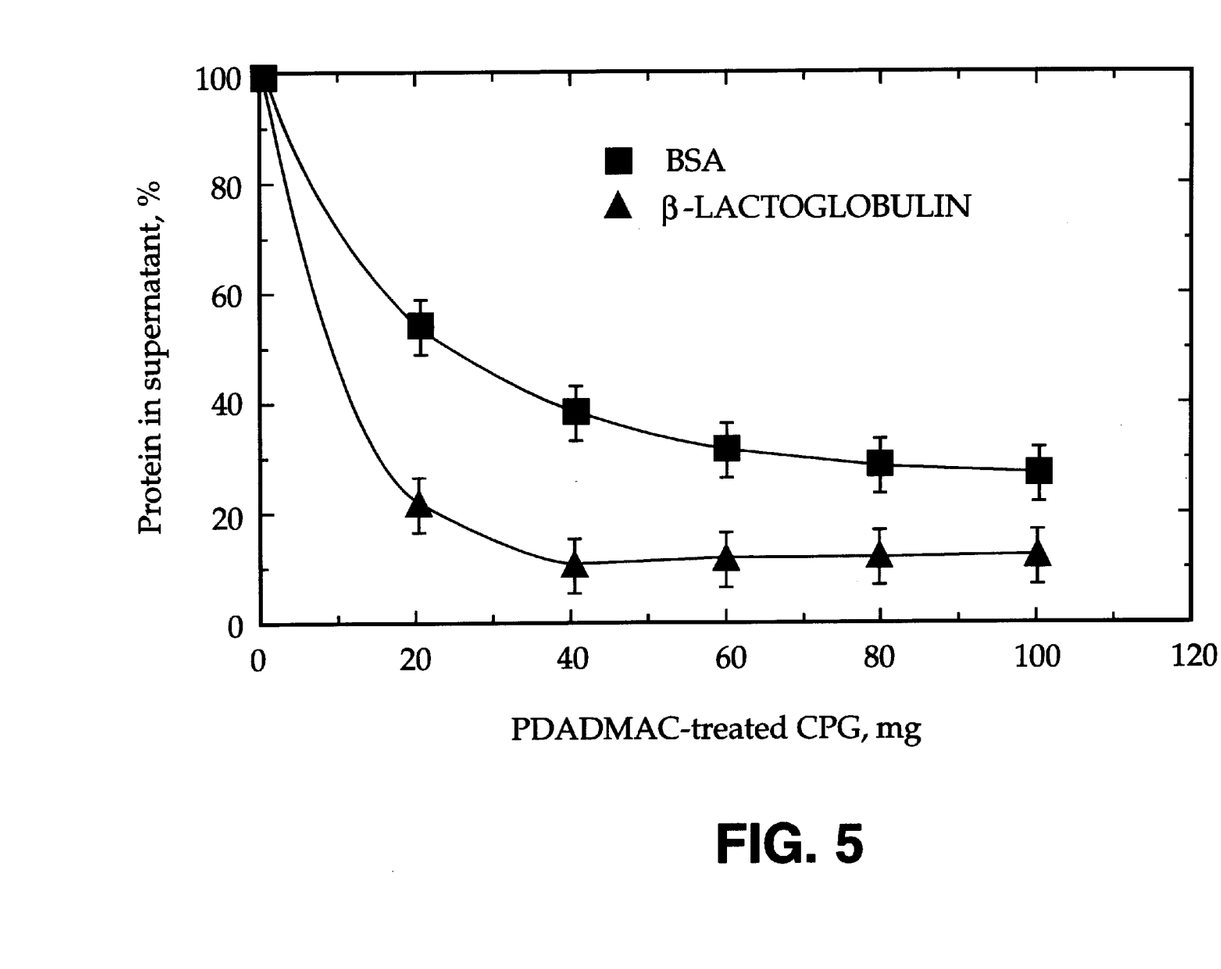
FIG. 5 is a graph of the removal efficiency for two different proteins as a function of PDADMAC concentration showing the optimum concentration level for selective protein removal by PDADMAC-CPG.

FIG. 5 [PDADMAC adsorption: pH 9.0, no salt added, Cp=20 g/L, stirring for 24 hours; Protein binding: pH'=9.0, I'=0.10, Cpr=0.10 g/L] reveals selective protein binding to polyelectrolyte-treated glass. β-Lactoglobulin (obtained from Sigma/Lot T1126) is more favorably bound to PDADMAC-CPG than BSA, consistent with the competitive removal of these proteins by coacervation with PDADMAC. Protein binding properties of PDADMAC in solution are thus retained after it is immobilized on the CPG surface.

Since the binding experiments are carried out under identical conditions, the dependence of protein removal on the foregoing variables must come from differences in the polyelectrolyte adsorption layer. The microscopic structure of the adsorbed polyelectrolyte affects subsequent protein binding.

EXAMPLE 7

Quasi-Elastic Light Scattering (QELS)

In order to establish a relationship between microscopic structure of adsorbed polyelectrolyte and protein binding, QELS testing was also used to study adsorbed polyelectrolyte layer thickness. Because CPG particles were too large to be studied by QELS, a model system consisting of small silica particles [KE-E10, Nippon Shokubai Co., Osaka, Japan were kindly supplied by Dr. Y. Morishima, Macromolecular Chemistry Dept., Osaka Univ.] and low molecular weight polyelectrolytes (L-120) were used.

PDADMAC (L-120, M$_n$=35,000) was a gift from Dr. H. Jaeger (Frauenhofer-Institut, Angewandte Polymerforschung, Germany). Adsorption on silica (KE-E10, 0.002 w/w %) particles was performed by slowly adding 0.002 w/w % PDADMAC into a solution of 0.2 w/w % silica at preadjusted pH and ionic strength. The solution was filtered through 0.45 micrometer whatman filters before light scattering measurement. The apparent stokes radius, R$_s$ of the PDADMAC-silica complex was determined by QELS with a Brookhaven (Holtsville, N.Y.) 72-channel BI-2030 AT digital correlator, using a 100 mW Argon ion laser. Standard procedures were used to obtain R$_s$ from the QELS results.

Figure 6:
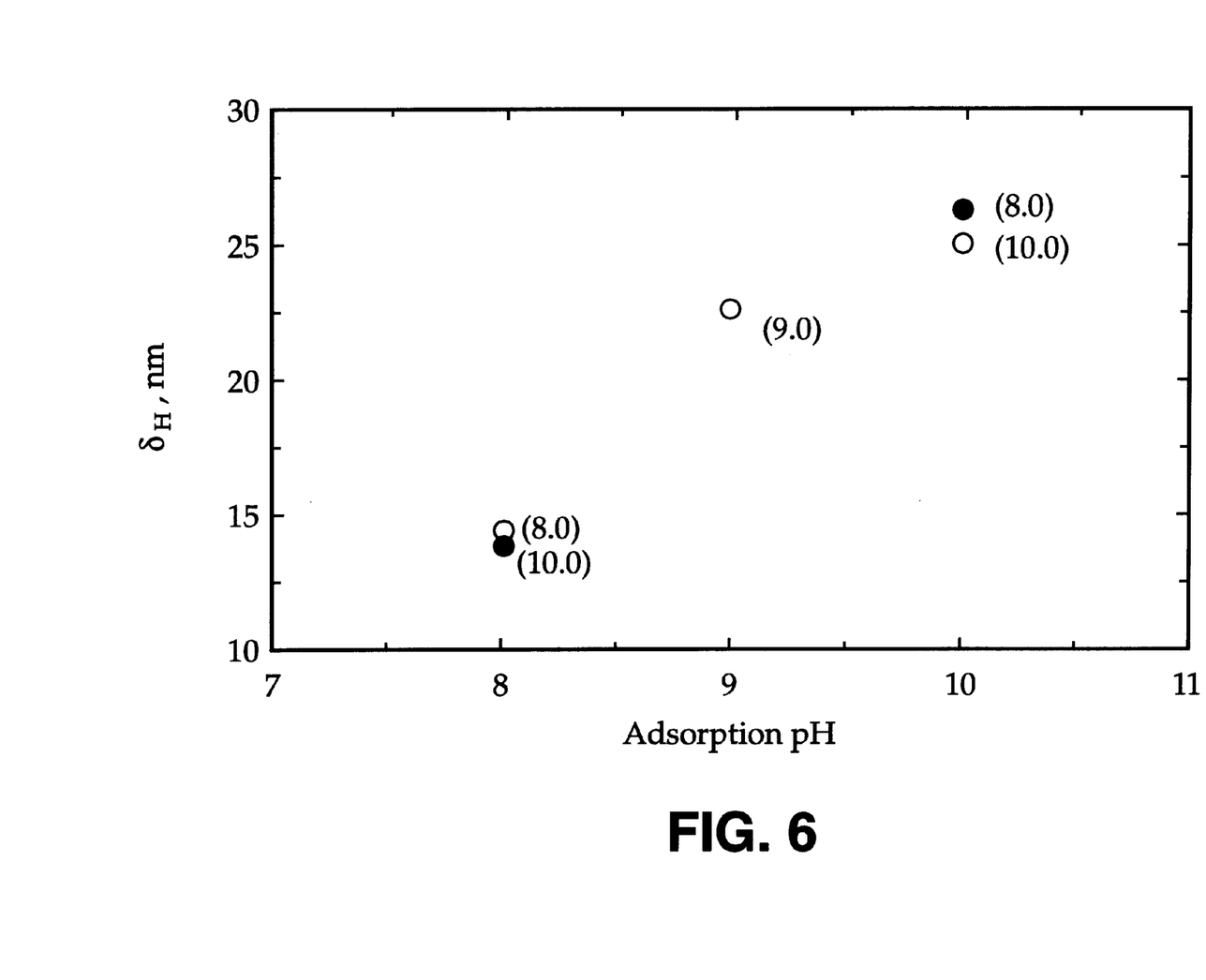
FIG. 6 is a graph of adsorption layer thickness as a function of adsorption pH.
Figure 7:
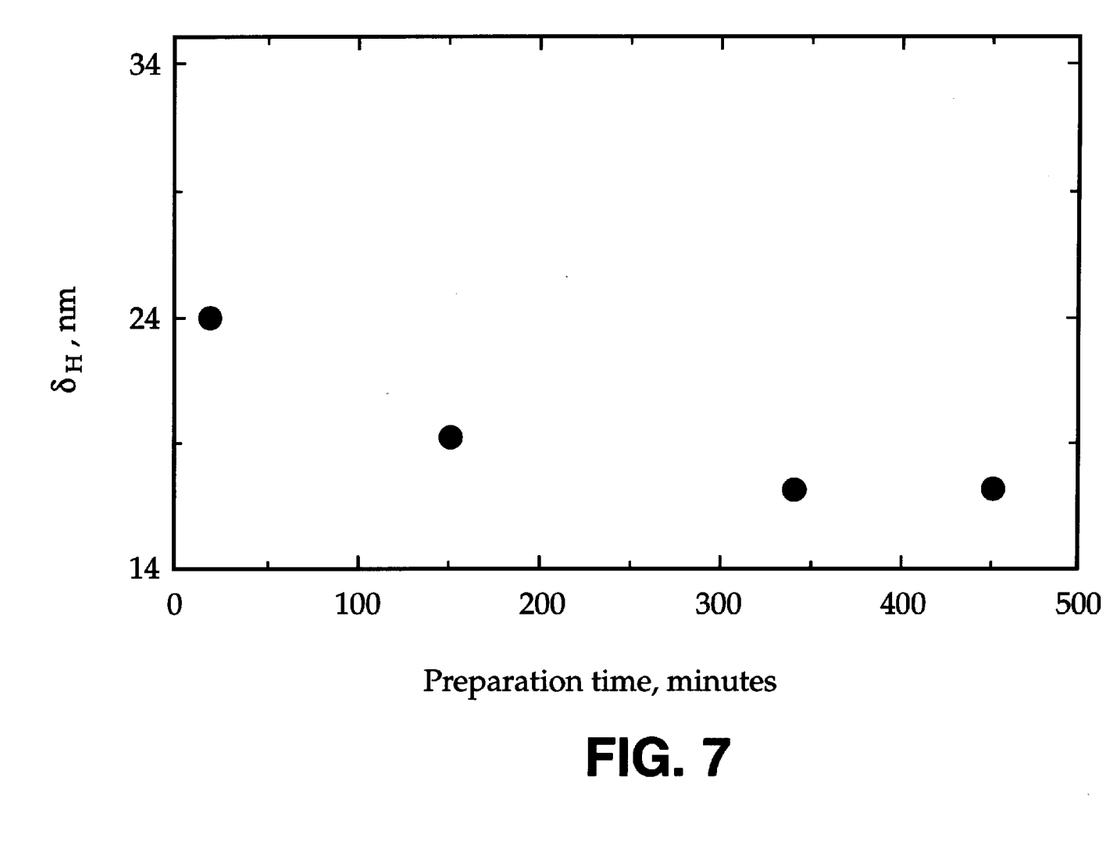
FIG. 7 is a graph of adsorption layer thickness as a function of mixing time.

The increase in the hydrodynamic radius of silica upon polyelectrolyte adsorption, taken as the adsorption layer thickness ($\delta_H$), is shown in FIG. 6 [(silica)=0.002 w/w %, (PDADMAC)=0.2 w/w %, I=0.01.] as a function of adsorption pH. In FIG. 6, the number in the brackets are the measuring pH, so that the filled circles represent results measured at pH other than adsorption conditions. The measurement pH has little influence on the result and the adsorption pH is the dominant factor. FIG. 7 [(silica)=0.002 w/w %, (PDADMAC)=0.2 w/w %, I=0.01.] shows the effect of mixing time in polyelectrolyte adsorption processes on $\delta_H$. At least 4 hours were required for adsorption to reach equilibrium. This observation demonstrates that polyelectrolyte adsorption is a slow process.

It is expected that protein binding depends on polyelectrolyte adsorption layer thickness. Therefore, QELS experiments were carried out to study the effect of ionic strength on $\delta_H$, and results are summarized in Table 1:

TABLE 1

Adsorption Layer Thickness ($\delta_H$) of PDADMAC (30K, 0.2 w/w %) on Silica (r = 50nm, 0.002 w/w %), pH = 9.0.

| | $\delta_H$, nm | | |
| | | I$_f$ = 0.01 M* | |
| I$_{i,M}$ | initial | 30 s | 23 hr. |
|---|---|---|---|
| 0 | 33 | 20 | 20 |
| 0.001 | 30 | 13 | — |
| 0.010 | 17 | — | — |

*After adjustment of ionic strength to 0.01.

Two important observations are shown in Table 1. First, $\delta_H$ was ionic strength dependent. Second the $\delta_H$ were different although they were measured under the same ionic strength as seen in column 3 of Table 1. This means that initial ionic strength is important for $\delta_H$. The decrease of $\delta_H$ may suggest that adsorbed chains partially collapsed upon increasing ionic strength.

Figure 8:
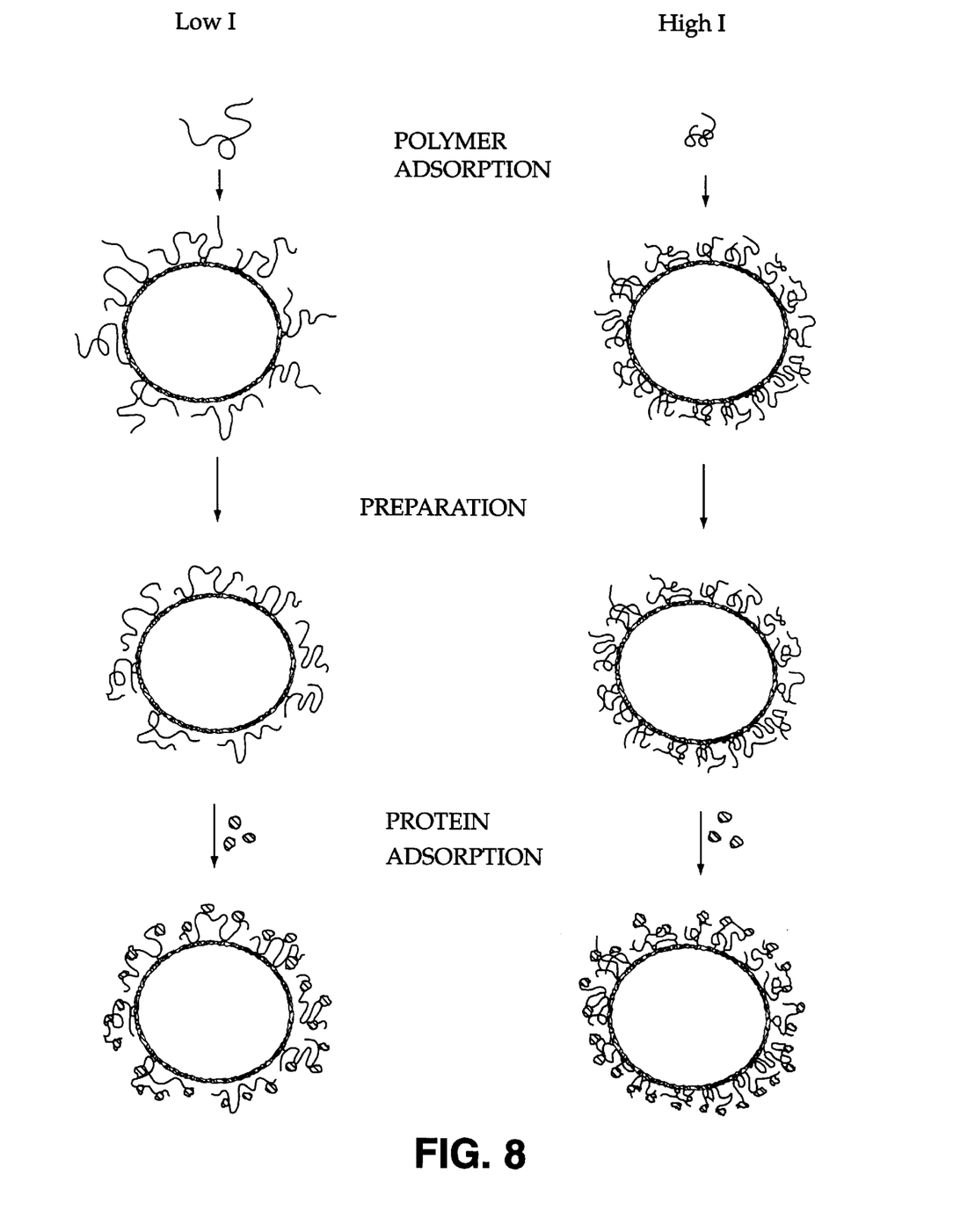
FIG. 8 schematically compares protein adsorption processes as a function of ionic strength.

The effect of pH on polyelectrolyte adsorption layer thickness and subsequent protein binding is illustrated schematically in FIG. 8. QELS results show that $\delta_H$ is increased with pH, as seen in FIG. 6, thus indicating that more binding sites are available for subsequent protein binding, which is verified by our protein binding experiment described above in relation to FIG. 3. Also the dependence of $\delta_H$ on preparation pH implies that protein binding would be a function of polyelectrolyte adsorption pH, which is also found in protein binding experiment as seen in FIG. 3.

Figure 9:
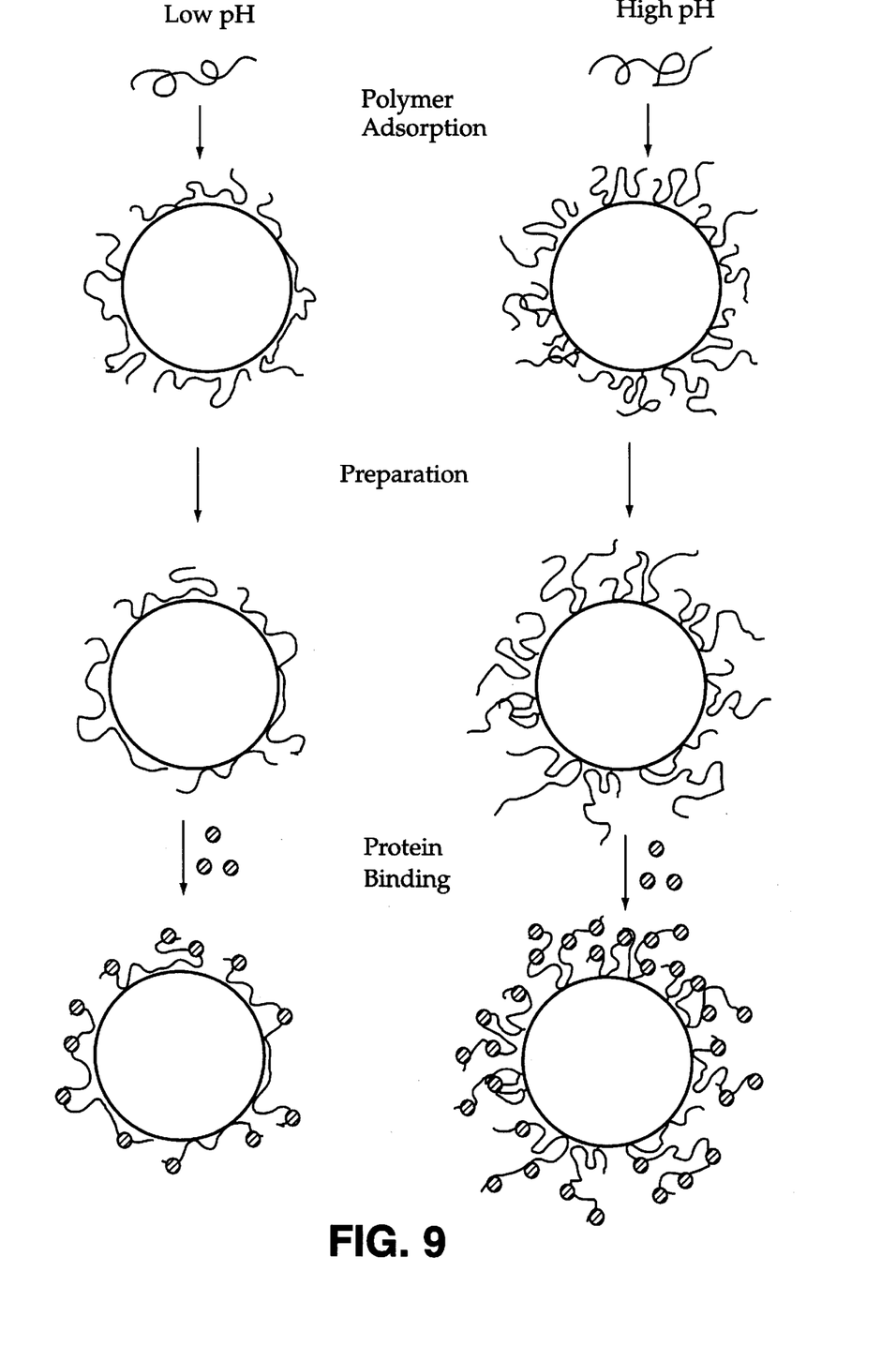
FIG. 9 schematically compares protein adsorption processes as a function of pH.

We suggest, as shown in FIG. 9, that polyelectrolytes will adopt different configurations when they are adsorbed at different ionic strengths. At low ionic strength, a loose structure of loops and tails will be formed on the CPG surfaces due to electrostatic repulsion between adsorbed chains. Each polymer chain could adsorb several protein molecules, as shown in FIG. 9. On the other hand, a compact structure of polyelectrolyte is formed at high ionic strength, and more polyelectrolyte molecules will be adsorbed. Although more polymer chains are adsorbed, proteins can only bind at peripherals. These two effects cancel each other. Therefore, ionic strength effect is less significant.

In conclusion, these results suggest that protein binding depends on the configurations of adsorbed polyelectrolytes, and the polyelectrolyte configurations are determined in polyelectrolyte adsorption stages. The big advantage of polyelectrolyte adsorption is the formation of loops and tails, which are controlled by the preparation conditions (pH, time, I). A properly designed polyelectrolyte-treated glass could be widely used in chromatographic separations.

While the preferred embodiments of the invention have been disclosed, it should be appreciated that the invention is susceptible to modification without departing from the spirit of the invention or the scope of the subjoined claims. For example, the present invention is not limited by the enzymes to be immobilized or the target proteins.

What is claimed is:

1. A material for selectively adsorbing predetermined proteins comprising:
   glass particles having a porous outer surface; and
   a permeable, polyelectrolyte layer, comprising at least one polymer having at least one cationic portion, provided on the surface of the glass particles, wherein the predetermined proteins can be selectively adsorbed on the polyelectrolyte layered glass particles.

2. The material of claim 1, wherein the glass particles have a size ranging from approximately 1 micron to approximately 1 millimeter in diameter.

3. The material of claim 1, wherein the polyelectrolyte layer forms on the glass particles in a thickness ranging from approximately 5 nanometers to approximately 20 nanometers.

4. The material of claim 1, wherein the cationic polyelectrolyte layer includes a polymer selected from the group consisting of poly(diallyldimethylammonium chloride) (PDADMAC), poly(methacrylamidopropyltrimethylammonium chloride) (PMAPTAC), poly(L-Lysine), poly(L-Arginine), poly(4-vinylpyridinium salt), polyethyleneimine (PEI), and combinations thereof.

5. The material of claim 1, wherein the polyelectrolyte layer includes a copolymer.

6. The material of claim 1, wherein the protein comprises an enzyme.

7. The material of claim 1, wherein the polyelectrolyte layer includes an anionic portion selected to attract the predetermined protein.

8. The material of claim 1, wherein the polyelectrolyte layer includes a nonionic portion selected to attract the predetermined protein.

9. The material of claim 1, wherein the polyelectrolyte layer includes a hydrophobic portion selected to attract the predetermined protein.

10. The material of claim 1, wherein the polyelectrolyte layer includes a hydrophilic portion selected to attract the predetermined protein.

11. A method for selectively immobilizing a predetermined enzyme comprising the steps of:

providing glass particles having a porous outer surface;

applying a permeable polyelectrolyte layer to the outer surface of the glass particles, wherein the polyelectrolyte comprises at least one polymer having at least one cationic portion; and supplying the predetermined enzyme in a manner which permits the enzyme to be adsorbed by the polyelectrolyte layered glass particles in order to immobilize the enzyme.

12. The method of claim 11, wherein the step of applying the polyelectrolyte layer includes restricting the application of the polyelectrolyte layer to a thickness ranging from 5 nanometers to approximately 20 nanometers.

13. The method of claim 11, wherein the step of providing glass particles includes restricting the glass particles to a size ranging from approximately 1 micron to approximately 1 millimeter in diameter.

14. The method of claim 11, wherein the step of applying the polyelectrolyte layer includes selecting at least one polymer having at least one portion selected to attract the predetermined protein and having a characteristic selected from the group consisting of the following general characteristics: hydrophobic, hydrophilic, anionic, nonionic, and desired combinations thereof.

15. A method for selectively separating a target protein from a medium having the target protein and one or more other components, comprising the steps of:

providing glass particles having a porous outer surface;

applying a permeable polyelectrolyte layer to the outer surface of the glass particles, wherein the polyelectrolyte comprises at least one polymer having at least one cationic portion; and supplying the polyelectrolyte layered glass particles to the medium in a manner to permit the predetermined protein to be selectively adsorbed by the polyelectrolyte layered glass particles.

16. The method of claim 15, wherein the step of applying a permeable polyelectrolyte layer includes restricting the application of the polyelectrolyte layer to a thickness ranging from approximately 5 nanometers to approximately 20 nanometers.

17. The method of claim 15, wherein the step of providing glass particles includes restricting the glass particles to a size ranging from approximately 1 micron to approximately 1 millimeter in diameter.

18. The method of claim 15, wherein the step of applying the polyelectrolyte layer includes selecting at least one polymer having at least one portion selected to attract the predetermined protein and having a characteristic selected from the group consisting of the following general characteristics: hydrophobic, hydrophilic, anionic, nonionic, and desired combinations thereof.

19. A method for making a material which can selectively adsorb a predetermined protein comprising the steps of:

adding one or more salt to water to provide a solution having an ionic strength ranging from approximately 0.01 molar to approximately 0.2 molar;

adding an acid or base, as needed, to maintain the pH of the solution within a range of from approximately 7.0 to approximately 10.0;

providing a polyelectrolyte to the solution, wherein the polyelectrolyte comprises at least one polymer having at least one cationic portion;

providing glass particles, having a porous outer surface, to the solution, wherein the polyelectrolyte is adsorbed on the outer surface of the glass particles; and separating the polyelectrolyte-treated glass particles from the solution.

20. The method of claim 19, further comprising the steps of washing and drying the separated polyelectrolyte treated glass particles to remove one or more excess materials selected from the group consisting of polymer, salt, acid, base, water or combinations thereof.

21. A material for selectively adsorbing predetermined proteins comprising:

silica particles; and a permeable, polyelectrolyte layer, comprising at least one polymer having at least one cationic portion, provided on the surface of the silica particles, wherein the predetermined proteins can be selectively adsorbed on the polyelectrolyte layered silica particles.

* * * * *